United States Patent [19]
Kyogoku et al.

[11] 4,085,135
[45] Apr. 18, 1978

[54] 2-(CARBOXYMETHOXY)-CHALCONES

[75] Inventors: Kazuaki Kyogoku, Tokyo; Katsuo Hatayama, Omiya; Sadakazu Yokomori, Ageo; Jiro Sawada; Ichiro Tanaka, both of Tokyo, all of Japan

[73] Assignee: Taisho Pharmaceutical Co., Ltd., Tokyo, Japan

[21] Appl. No.: 767,974

[22] Filed: Feb. 11, 1977

[30] Foreign Application Priority Data

Feb. 13, 1976 Japan .................................. 51-14578

[51] Int. Cl.$^2$ ........................................... C07C 65/22
[52] U.S. Cl. .................................. 260/520 C; 424/317
[58] Field of Search .................................... 260/520 C

[56] References Cited
U.S. PATENT DOCUMENTS 3,255,241  6/1966  Schultz et al. .................. 260/520 C
3,928,421  12/1975  Kyogoku et al. ................ 260/520 C Primary Examiner—Jane S. Myers
Attorney, Agent, or Firm—Wenderoth, Lind & Ponack

[57] ABSTRACT

Novel 2'-(carboxymethoxy)-chalcones of the formula

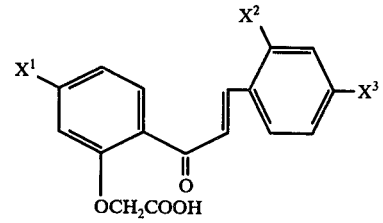

wherein one or two of $X^1$, $X^2$ and $X^3$ are 3-methyl-2-butenyloxy and the other or others are hydrogen, possess excellent antigastric and anti-duodenal ulcer activities, together with a high absorptive ratio in the living body and low acute and chronic toxicity.

7 Claims, No Drawings

2-(CARBOXYMETHOXY)-CHALCONES

FIELD OF INVENTION

This invention relates to 2'-(carboxymethoxy)-chalcones, having anti-gastric and anti-duodenal ulcer activities, and a process for their preparation.

DESCRIPTION OF PRIOR ART

Various chalcones are reported to have some utility, such as oxidation inhibitor, radiation absorbent and sweetening agent, and some chalcones are reported to be pharmacologically active, for example, as analgesic, anti-inflammatory, anti-bacterial and vasodilator agents.

There are some reports of chalcones having anti-gastric ulcer activity, as follows:

Sophoradochromene: Japanese Pat. No. 623498;

2, 2', 4, 4'-Tetrahydroxy-6'-methoxy-3'-(5-methyl-2-isopropenylhex-4-enyl)-chalcone : Japanese Pat. No. 691783;

Isoliquiritigenin : Arzneimittel Forschung 17, 1544 (1967); and

Anti-Gastric Ulcer Chalcone Ethers : U. S. Pat. No. 3928421.

The above Japanese Patents disclose methods of extracting compounds from plants, which methods are accompanied by disadvantages such as complicated procedure, low yield and low purity.

The above-mentioned isoliquiritigenin is obtained by hydrolyzing isoliquiritin, extracted from plant with low yield.

All of the above-mentioned chalcones have only a few or no hydrophilic groups, so that a good absorptive ratio in the living body cannot be expected.

Chalcone derivatives having anti-duodenal ulcer activity have not yet been prepared.

BRIEF SUMMARY OF INVENTION

The object of the present invention is to provide novel chalcone derivatives possessing excellent anti-gastric and anti-duodenal ulcer activities, together with a high absorptive ratio in the living body and low acute and chronic toxicity.

A further object of this invention is to provide these chalcone derivatives by a simple and convenient procedure, especially by a process which is readily applicable to production on a commerical scale.

Thus, this invention relates to novel 2'-(carboxymethoxy)-chalcones, more particularly, 2'-(carboxymethoxy)-chalcones of the formula (I)

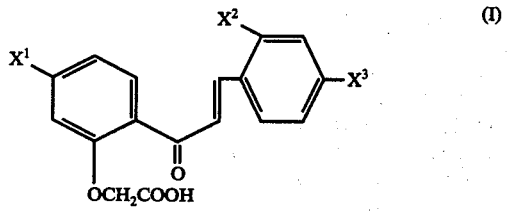

(I)

wherein one or two of $X^1$, $X^2$ and $X^3$ are 3-methyl-2-butenyloxy, and the other or others are hydrogen.

The compounds (I) show a high absorptive ratio in the living body and also remarkable anti-gastric and anti-duodenal ulcer activities, which have not been observed in any other previously known anti-gastric ulcer chalcones. That is, the compounds (I) show excellent effect for treating acetic acid ulcers, which are analogous to chronic gastric ulcers, as well as for treating various kinds of other gastric ulcers such as stress ulcers, Shay's ulcers, histamine ulcers, and ulcers induced by drugs, for example, aspirin and anti-inflammatory agents. Moreover, the compounds (I) show a remarkable effect for treating cysteamine ulcers, which can take the form of either a duodenal ulcer or a gastric ulcer.

These merits of the compounds (I), that is, high absorptive ratio, excellent anti-gastric and anti-duodenal ulcer activities and low toxicity, are considered to be attributed to the combination of chalcone parent structure, the 2'-carboxymethoxy group and the 3-methyl-2-butenyloxy group or groups. The high absorptive ratio is especially attributed to the 2'-carboxymethoxy group.

DETAILED DESCRIPTION OF INVENTION

The compounds (I) can be prepared by the following reaction:

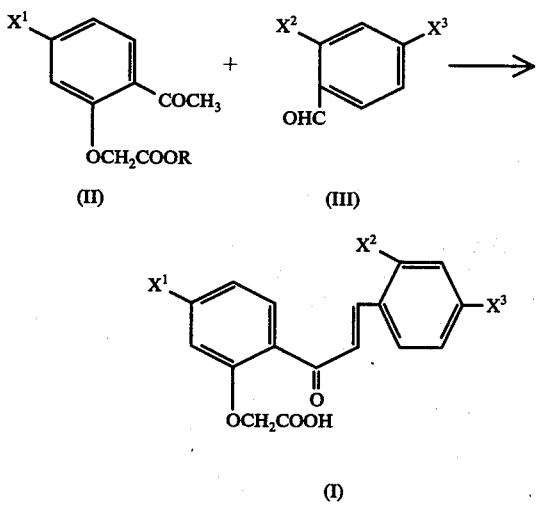

wherein $X^1$, $X^2$ and $X^3$ are the same as defined above, and R is hydrogen or alkyl containing 1 to 6 carbon atoms.

Reaction of the compounds (II) and (III) can be carried out by adding an alkali, such as sodium hydroxide, potassium hydroxide, soduim carbonate or potassium carbonate, to a solution of the compounds (II) and (III) in an organic solvent, such as methanol, ethanol, acetone, hexane or dimethylformamide, and agitating the mixture for 2–5 hours at 0°–100° C. The compound (I) can be separated from the mother liquor and purified by recrystallization.

The compound (II) can be prepared by reaction of 2-hydroxyacetophenone or 2-hydroxy-4-(3-methyl-2-butenyloxy) acetophenone with halogenoacetic acid or halogenoacetic acid lower alkyl ester, while the compound (III) can be prepared by reaction of 2-hydroxybenzaldehyde, 4-hydroxybenzaldehyde or 2,4-dihydroxybenzaldehyde with 1-halogeno-3-methyl-2-butene.

The compounds (I) show a higher absorptive ratio in rats than the compounds which have no 2'-carboxymethoxy group, as shown in Table I.

As also indicated in Table I, the compounds (I) show excellent effects in treating and preventing various types of experimental gastric ulcers in rats and guinea pigs. That is, the present compounds accelerated the healing process of chronic gastric ulcers induced by injection of acetic acid (Acetic acid ulcer), inhibited ulcers and erosions formed by ligation of pylorus (Shay's ulcer) or by stressing animals by means of restraint and water immersion (Stress ulcer), and also inhibited ulcers and erosions induced by administration of aspirin (Aspirin ulcer). The compounds (I) also accelerated the healing process of acute gastric ulcers induced by injection of histamine (Histamine ulcer). Moreover, the compounds (I) inhibited ulcers and erosions induced by administration of cysteamine (Cysteamine ulcer), not only with respect to gastric ulcers, but also with respect to duodenal ulcers and erosions. None of these effects were found in the chalcones lacking the 2'-carboxymethoxy group, as also shown in Table I.

The compounds (I) are effective in treating both acute and chronic gastric ulcers, accelerate reparation of injured gastric mucosal tissue, aid in preventing gastric ulcers from occuring or from recurring, and exhibit excellent healing effects toward previously existing gastric ulcers, and are also effective in treating duodenal ulcers. Further, although the present compounds have weak suppresive activity toward secretion of factors which are aggresive to ulcers, such as hydrochloric acid or pepsin, they do not show such side effects as are observed in the administration of anti-cholinergic drugs.

In terms of general pharmacological activity, no unfavorable side effects have yet been observed in the central nervous system or autonomic nervous system following administration of the present compounds.

The toxicity of the compounds (I) is extremely low. Death was not observed within 96 hours in mice, rats or dogs following administration of 8 g/kg orally, and no side effect was observed after administration of 1 g/kg/day orally for 30 days, and it is therefore apparent that the compounds can be administered safely over a long period of time without accompanying side effects.

The compounds (I) may be administered orally or parenterally for treatment of gastric and duodenal ulcers, gastric hyperacidity, acute and chronic gastritis, chronic constipation, chronic diarrhea, hypogastralgia and any other gastric ailment. The dosage for humans is 10–150 mg/day.

The following reference examples relate to preparation of compounds (II) and (III).

Reference Example 1

To a solution of 1.1 g of 2-hydroxy-4-(3-methyl-2-butenyloxy)-acetophenone in 20 ml of acetone, 0.3 g of potassium hydroxide was added, and to the mixture 1.0 g of bromoacetic acid ethyl ester was added dropwise while stirring. The mixture was agitated for 2 hours at room temperature. The reaction mixture was acidified with dilute hydrochloric acid, and extracted with ether three times. The ether layer was washed well with water and dried over Na$_2$SO$_4$. Evaporation of ether left a residue, which was recrystallized from ether-petroleum benzine, giving 1.4 g of 2-(ethoxycarbonylmethoxy)-4-(3-methyl-2-butenyloxy)-acetophenone, m.p. 60°–62° C.

Reference Example 2

Bromoacetic acid ethyl ester of Reference Example 1 was substituted by chloroacetic acid methyl ester, and the same procedure was carried out to give 1.3 g of 2-(methoxycarbonylmethoxy)-4-(3-methyl-2-butenyloxy)-acetophenone, m.p. 80°–82° C.

Reference Example 3

Bromoacetic acid ethyl ester of Reference Example 1 was substituted by bromoacetic acid, and the same procedure was carried out to give 0.9 g of 2-(carboxymethoxy)-4-(3-methyl-2-butenyloxy)-acetophenone, m.p. 138°–140° C.

Reference Example 4

To a solution of 10 g of 2-hydroxyacetophenone in 40 ml of acetone, 12 g of potassium carbonate was added, and after the mixture was agitated for 1 hour at room temperature, 14 g of bromoacetic acid ethyl ester was added dropwise while stirring, and the resultant mixture was agitated for 3 hours. The reaction mixture was filtered and acetone was evaporated, leaving a residue which was extracted with ether. Evaporation of ether left a residue, which was recrystallized from petroleum ether to give 9.7 g of 2-(ethoxycarbonylmethoxy)-acetophenone, m.p. 33°–35° C.

Reference Example 5

To a solution of 5 g of 2,4-dihydroxybenzaldehyde in 200 ml of acetone, 15 g of potassium carbonate was added, and after the mixture was agitated for 20 minutes at room temperture, 12 g of 3-methyl-2-butenyl bromide was added dropwise while stirring, and the resultant mixture was agitated for 3 hours. The reaction mixture was filtered and acetone was evaporated, leaving a residue which was dissolved in ether. To the ether solution 2% sodium hydroxide solution was added, and the ether layer was washed with water and dried over Na$_2$SO$_4$. Evaporation of ether left 9 g of 2,4-bis-(3-methyl-2-butenyloxy)-benzaldehyde as an oily product.

The following examples relate to preparation of the compounds of the present invention.

EXAMPLE 1

To a solution of 1.5 g of 2-(ethoxycarbonylmethoxy)-4-(3-methyl-2-butenyloxy)-acetophenone and 1.0 g of 4-(3-methyl-2-butenyloxy)-benzaldehyde in 5 ml of ethanol, 10 ml of 20% potassium hydroxide solution was added, and the solution was agitated for 4 hours at room temperature. The reaction mixture was acidified with dilute hydrochloric acid, and the resultant precipitate was washed with water. Recrystallization from ethanol gave 1.7 g of light yellow needles, 2'-(carboxymethoxy)-4,4'-bis-(3-methyl-2-butenyloxy)-chalcone, m.p. 141°–142° C.

EXAMPLE 2

To a solution of 1.5 g of 2-(methoxycarbonylmethoxy)-4-(3-methyl-2-butenyloxy)-acetophenone and 1.0 g of 2-(3-methyl-2-butenyloxy)-benzaldehyde in 10 ml of ethanol, 10 ml of 20% potassium hydroxide solution was added, and the solution was refluxed for 2 hours. The reaction mixture was acidified with dilute hydrochloric acid, and extracted with ether. Evaporation of ether left a residue, which was recrystallized from ethanol, giving 1.7 g of light yellow needles, 2,4'-bis-(3-methyl-2-butenyloxy)-chalcone, m.p. 78°–80° C.

EXAMPLE 3

To a solution of 2.3 g of 2-(carboxymethoxy)-4-(3-methyl-2-butenyloxy)-acetophenone and 0.8 g of benzaldehyde in 10 ml of ethanol, 15 ml of 50% potassium hydroxide solution was added, and the solution was agitated for 3 hours at 25° C. The reaction mixture was acidified with dilute hydrochloric acid to give yellow crystals, which were washed with water. Recrystallization from n-hexane-benzene gave 2.0 g of yellow needles, 2'-(carboxymethoxy)-4'-(3-methyl-2-butenyloxy)-chalcone, m.p. 112°–114° C.

EXAMPLE 4

To a solution of 1.0 g of 2-(ethoxycarbonylmethoxy)-acetophenone and 1.2 g of 2,4-bis-(3-methyl-2-butenyloxy)-benzaldehyde in 30 ml of ethanol, 7 ml of 50% potassium hydroxide solution was added, and the solution was agitated for 4 hours at room temperature. The reaction mixture was acidified with dilute hydrochloric acid, and extracted with ether. Evaporation of ether left a residue, which was recrystallized from benzene to give 1.5 g of light yellow needles, 2'-(carboxymethoxy)-2,4-bis-(3-methyl-2-butenyloxy)-chalcone, m.p. 81°–83° C.

EXAMPLE 5

To a solution of 1.5 g of 2-(ethoxycarbonylmethoxy)-acetophenone and 1.3 g of 4-(3-methyl-2-butenyloxy)-benzaldehyde in 17 ml of ethanol, 17 ml of 50% potassium hydroxde solution was added, and the solution was agitated for 5 hours at room temperature. The reaction mixture was acidified with dilute hydrochloric acid to precipitate an oily substance, which was washed with water and then extracted with ether. Evaporation of ether left a residue, which was recrystallized from benzene to give 1.1 g of yellow needles, 2'-(carboxymethoxy)-4-(3-methyl-2-butenyloxy)-chalcone, m.p. 141°–142° C.

EXAMPLE 6

To a solution of 1.2 g of 2-(ethoxycarboynlmethoxy)-aceptophenone and 1.0 g of 2-(3-methyl-2-butenyloxy)-benzaldehyde in 25 ml of ethanol, 7 ml of 50% potassium hydroxide solution was added, and the solution was agitated for 2 hours at 50° C. The reaction mixture was acidified with dilute hydrochloric acid, and extracted with ether. Evaporation of ether left a residue, which was recrystallized from n-hexane-benzene to give 1.5 g light yellow needles, 2'-(carboxymethoxy)-2-(3-methyl-2-butenyloxy)-chalcone, m.p. 80°–81° C.

The following tests illustrate biological assay procedures for determining absorptive ratio and physiological activities.

Test I

Male rats of Wistar strain were deprived of food for 24 hours, and under ether anesthesia the abdominal wall was incised along the midline. Then, the pylorus and 4 cm distal portion from the pylorus were respectively ligated to make blind sack. The test solution (100 mg/kg of test drug suspended in 0.5% carboxymethylcellulose-Na solution) was injected into this sack. Three hours after dosing, the sack was removed and the amount of drug remaining was measured for the determination of absorptive ratio of the test drug.

Test II

Anti-gastric ulcer activity of the present compounds was tested according to Takagi's acetic acid ulcer method (Japanese Journal of Pharmacology, 19, 418 (1969)).

Male rats of Donryu strain weighing 230 to 250 g were used for testing the curative effect of the present compounds on chronic gastic ulcers induced by means of submucosal injection of acetic acid.

Animals were laparotomized under ether anesthesia and injected with 0.01 ml of 20% acetic acid between the serosa and the muscular layer of the pyloric antrum. After surgery, the abdomen was closed and the animals were fed normally. The test drugs were perorally administered twice a day for ten days, from two days after the operation, and the animals were sacrificed at the twelfth day from the operation in order to assess the healing process of the ulcer. Each stomach was removed, filled with 15 ml of 1% formalin solution and placed in the same solution for about 10 minutes to fix the outer layer of the gastric wall, according to Brodie's method (Gastroenterology, 38, 353 (1960)).

Then, the stomach was cut open along the greater curvature and the lesions in the stomach were observed. The area of the ulcer was designated as the ulcer index.

Using the ulcer index, the curative ratio of the ulcer was calculated from the following equation:

$$\text{Curative ratio (\%)} = 100(C-S)/C,$$

wherein C is the ulcer index of the control, and S is the ulcer index of the test compound.

In Table I, the curative ratio of each test compound is shown.

Test III

Another anti-gastric ulcer activity test was conducted by Shay's ulcer method (Gastroenterology, 5, 43 (1945)).

Male rats of Donryu strain weighing 200 to 230 g were used for testing the preventive effect of the present compounds toward so-called Shay's ulcer, produced by ligation of the pylorus. Preceding the operation, the animals were fasted for 48 hours, except for water ad libitum. Under ether anesthesia, the mid ventral line of the animal was incised and the pylorus was ligated. Then, the abdomen was closed and the test drugs were administered intra-peritoneally. 15 hours after the operation the animals were sacrificed by ether inhalation. The esophagus was ligated and the stomach was carefully removed. The volume of gastric juice was measured and the lesions at the portion of the forestomach were macroscopically examined. The areas of ulcers and erosions were measured and the sum of both was designated as the ulcer index.

Using the ulcer index, the preventive ratio was calculated from the following equation:
$$\text{Preventive ratio (\%)} = 100(C-S)/C,$$

wherein C is the ulcer index of the control, and S is the ulcer index of the test compound.

In Table I, the ulcer index for each compound is shown, together with the preventive ratio of gastric juice secretion (%), which was calculated in the same manner as the preventive ratio of the ulcer.

Test IV

Anti-gastric ulcer activity of the present compounds was investigated by Takagi's stress ulcer method (Japanese Journal of Pharmacology, 18, 9 (1968)).

Male rats of Donryu strain weighing 260 to 300 g were used for testing the preventive effect of the present compounds to gastric ulcer produced by means of restraint and water immersion. Animals were placed and immobilized in the stress cage and immersed vertically to the xyphoid of the animal in a water bath at 23° C for 7 hours. The test drugs were intra-peritoneally administered 30 minutes before restraint.

At the end of the stress period, the animals were removed from water bath, released from the stress cage and sacrificed by a blow. The stomach was removed and inflated with 15 ml of 1% formalin solution and placed in the same solution for about 10 minutes to fix the outer layer of the gastric wall according to Brodie's method. Then, the stomach was cut open along the greater curvature and lesions were examined macroscopically. The areas of the ulcers and erosions were measured and the sum of both was designated as the ulcer index.

From the equation described in Test III, each preventive ratio (%) was calculated and indicated in Table I.

Test V

Selecting aspirin as a drug which often brings about gastric ulcers, anti-gastric ulcer activity of the present compounds was investigated.

Male rats of Donryu strain weighing 200 to 300 g were used for the examination of preventive effect to aspirin-induced gastric ulcers.

Animals were treated by administering to each 200 mg/kg of aspirin perorally, three times, at 2 hour intervals. The test drugs were perorally administered 30 minutes before the initial aspirin administration, the animals were sacrificed by a blow and each stomach was removed and inflated with about 15 ml of 1% formalin solution and placed in 1% formalin solution. Ten minutes later, the stomach was cut open along the greater curvature and the areas of ulcers and erosions were measured. The sum of both was designated as the ulcer index and each preventive ratio (%) was calculated in the same manner as described in Test III and is shown in Table I.

Test VI

Anti-gastric ulcer activity of the present compounds was investigated by the Histamine ulcer method.

Male guinea pigs of Hartley strain weighing 360 to 400 g were deprived of food for 24 hours and given histamine hydrochloride (50 mg/kg) subcutaneously 15 minutes after intramuscular tripelenamine hydrochloride (10 mg/kg) dosing. Then, the animals were orally given 100 mg/kg/day of the test drug suspended in 0.4% carboxymethylcellulose-Na solution for three days. The animals were sacrificed by a blow on the head on the 4th day after the treatment for ulceration. After 1% formalin treatment, the stomach was incised along the greater curvature and the lesions in the stomach were observed.

From the equation described in Test II, each curative ratio (%) was calculated and is indicated in Table I.

Test VII

Anti-gastric and anti-duodenal ulcer activities of the preset compounds were investigated by the Cysteamine ulcer method.

Male rats of Donryu strain weighing 200 to 220 g were deprived of food for 24 hours and given cysteamine hydrochloride (400 mg/kg) subcutaneously 30 minutes after oral administration of the test drug. The animals were sacrificed 18 hours after test drug dosing, and the stomach was examined for gastric and duodenal ulcers. Ulcer index was expressed as the total area ($mm^2$) damaged.

From the equation described in Test III, each preventive ratio (%) was calculated and indicated in Table I.

| Compound (I) | Absorptive Ratio (%) | Dose (mg/kg) | Curative Ratio (%) of | | Prevention Ratio (%) of | | | Cysteamine Ulcer | | Gastric Juice Secretion in the Case of Shay's Ulcer |
| | | | Acetic Acid Ulcer | Histamine Ulcer | Shay's Ulcer | Stress Ulcer | Aspirin Ulcer | Gastric Ulcer | Duodenal Ulcer | |
| --- | --- | --- | --- | --- | --- | --- | --- | --- | --- | --- |
| Example 1 | 52.2 | 100 | 76.1 | 58.5 | 95.2 | 89.6 | 63.3 | 91.1 | 61.1 | 31.1 |
| | | 50 | 75.1 | 40.2 | 91.5 | 84.2 | 61.8 | 88.9 | 57.1 | 30.8 |
| | | 20 | 56.2 | 31.4 | 87.2 | 70.1 | 55.3 | 64.4 | 47.0 | 27.2 |
| Example 2 | 51.8 | 100 | 67.3 | 55.8 | 78.6 | 87.5 | 62.6 | 90.6 | 62.2 | 30.0 |
| | | 50 | 62.1 | 39.9 | 77.7 | 81.9 | 60.6 | 88.5 | 56.3 | 27.5 |
| | | 20 | 55.2 | 30.3 | 75.4 | 71.1 | 54.1 | 65.8 | 61.3 | 25.7 |
| Example 3 | 63.7 | 100 | 66.5 | 52.7 | 87.6 | 78.8 | 52.2 | 89.8 | 53.4 | 29.9 |
| | | 50 | 60.3 | 35.6 | 85.1 | 76.2 | 53.4 | 82.0 | 47.8 | 34.1 |
| | | 20 | 45.8 | 25.4 | 80.4 | 69.8 | 47.2 | 76.6 | 42.1 | 26.6 |
| Example 4 | 50.6 | 100 | 61.1 | 48.5 | 94.0 | 86.2 | 59.6 | 88.8 | 58.8 | 29.1 |
| | | 50 | 59.8 | 37.8 | 89.6 | 79.8 | 54.6 | 83.2 | 55.5 | 30.4 |
| | | 20 | 55.2 | 31.1 | 79.7 | 68.3 | 52.2 | 81.5 | 46.4 | 24.5 |
| Example 5 | 65.3 | 100 | 61.8 | 46.8 | 87.3 | 78.8 | 54.7 | 87.5 | 51.3 | 29.6 |
| | | 50 | 61.3 | 36.8 | 79.9 | 73.3 | 49.5 | 67.9 | 45.8 | 18.9 |
| | | 20 | 52.7 | 27.8 | 75.7 | 65.5 | 43.1 | 65.3 | 43.5 | 19.6 |
| Example 6 | 64.2 | 100 | 59.7 | 25.5 | 81.3 | 76.9 | 55.2 | 86.9 | 52.1 | 27.8 |
| | | 50 | 59.6 | 24.2 | 79.6 | 67.6 | 48.9 | 78.9 | 48.4 | 20.4 |
| | | 20 | 47.8 | 22.4 | 75.5 | 58.9 | 44.0 | 72.1 | 39.9 | 23.1 |
| Compound A | 3.7 | 100 | 71.1 | 2.5 | 74.2 | 76.7 | 51.1 | 4.8 | 5.1 | 29.9 |
| | | 50 | 57.4 | — | 76.7 | 51.1 | 37.9 | — | — | 25.4 |
| | | 20 | 27.6 | — | 31.2 | 48.5 | 25.6 | — | — | 19.1 |
| Compound B | 3.1 | 100 | 55.7 | 3.3 | 79.3 | 78.8 | 8.7 | 5.2 | 6.3 | 27.7 |
| | | 50 | 47.0 | — | 68.2 | 63.2 | — | — | — | 28.5 |
| | | 20 | 18.0 | — | 38.1 | 42.4 | — | — | — | 25.8 |

Compound A : 4,4'-bis-(3-methyl-2-butenyloxy)-chalcone
Compound B : 2'-methoxy-4,4'-bis-(3-methyl-2-butenyloxy)-chalcone

What we claim is:
1. A compound of the formula

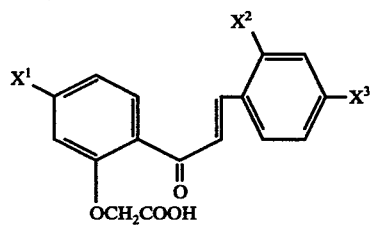

wherein one or two of $X^1$, $X^2$ and $X^3$ are 3-methyl-2-butenyloxy, and the other or others of $X^1$, $X^2$ and $X^3$ are hydrogen.

2. The compound according to claim 1, namely, 2'-(carboxymethoxy)-4,4'-bis-(3-methyl-2-butenyloxyl)-chalcone.

3. The compound according to claim 1, namely, 2'-(carboxymethoxy)-2,4'-bis-(3-methyl-2-butenyloxy)-chalcone.

4. The compound according to claim 1, namely, 2'-(carboxymethoxy)-4'-(3-methyl-2-butenyloxy)-chalcone.

5. The compound according to claim 1, namely, 2'-(carboxymethoxy)-2,4-bis-(3-methyl-2-butenyloxy)-chalcone.

6. The compound according to claim 1, namely, 2'-(carboxymethoxy)-4-(3-methyl-2-butenyloxy)-chalcone.

7. The compound according to claim 1, namely, 2'-(carboxymethoxy)-2-(3-methyl-2-butenyloxy)-chalcone.

* * * * *